United States Patent
Bramucci et al.

(10) Patent No.: US 6,562,603 B2
(45) Date of Patent: May 13, 2003

(54) 3-HYDROXYCARBOXYLIC ACID PRODUCTION AND USE IN BRANCHED POLYMERS

(75) Inventors: Michael G. Bramucci, Folsom, PA (US); Robert Dicosimo, Rockland, DE (US); Robert Fallon, Elkton, MD (US); John E. Gavagan, Wilmington, DE (US); Frank Herkes, Wilmington, DE (US); Lech Wilczek, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/921,260

(22) Filed: Aug. 2, 2001

(65) Prior Publication Data

US 2002/0039770 A1 Apr. 4, 2002

Related U.S. Application Data

(60) Provisional application No. 60/223,044, filed on Aug. 4, 2000.

(51) Int. Cl.$^7$ .................................................. C12P 7/42
(52) U.S. Cl. ........................ 435/146; 435/170; 435/227; 435/232
(58) Field of Search ............................... 435/146, 227, 435/232, 170

(56) References Cited

U.S. PATENT DOCUMENTS

| | | |
|---|---|---|
| 3,553,081 A | 1/1971 | Goodhue et al. |
| 5,334,519 A | 8/1994 | Nitto |
| 5,998,180 A | 12/1999 | Ciba |

FOREIGN PATENT DOCUMENTS

| | | |
|---|---|---|
| CA | 2103616 | 2/1994 |
| DE | 19848129 A1 | 4/2000 |
| EP | 0502476 A2 | 9/1992 |
| JP | 59053838 B2 | 12/1984 |
| WO | WO 9118995 A1 | 12/1991 |
| WO | WO 9712964 A2 | 4/1997 |
| WO | WO 9744318 A1 | 11/1997 |
| WO | WO 9929889 A1 | 6/1999 |
| WO | WO 0164857 A1 | 9/2001 |

OTHER PUBLICATIONS

Raadt et al "Chemoselective Enzymatic Hydrolysis of Aliphatic and Alicyclic Nitriles" J. Chem Soc. Perkin Trans 1 1992 pp. 137–140.*

Hult et al., pp. 656–658, Concise Polymeric Materials Encyclopedia, ed. J. C. Salomone, CRC Press, New York, 1999.

Voit et al., pp. 658–659, Concise Polymeric Materials Encyclopedia, ed. J. C. Salomone, CRC Press, New York, 1999.

Goodman, PP. 793–799, Concise Encyclopedia of Polymer Science and Engineering, ed. J. I. Kroschwitz, John Wiley & Sons, New York, 1990.

Hasegawa et al., J. Ferment. Technol. 59: 257–262, 1981.

Seebach et al., Helv. Chim. Acta 77: 2007–2034, 1994.

Bayer et al., Appl. Microbiol. Biotechnol. 42: 543–547, 1994.

Burk et al., Organometallics 9: 2653–2655, 1990.

Sugai et al., Biosci. Biotech. Biochem. 61: 1419–1427, 1997.

Asano et al., Agric. Biol. Chem. 44: 2497–2498, 1980.

De Raadt et al., J. Chem. Soc. Perkin Trans. 1, pp. 137–140, 1992.

Cramp et al., Biochem. Biophys. Acta 1431: 249–260, 1999.

Tetrahedron 46: 5587–5590, 1990.

Kobayashi et al., J. Bacteriology 172: 4807–4815, 1990.

Levy–Schil et al., Gene 161: 15–20, 1995.

Bengis–Garber et al., Appl. Microbiol. Biotechnol. 32: pp. 11–16, 1989.

Gradley et al., Biotechnology Lett. 16: pp. 41–46, 1994.

Bhalla et al., Appl. Microbiol. Biotechnol. 37: 184–190, 1992.

Goldlust et al., Biotechnol. Appl. Biochem. 11: pp. 581–601, 1989.

Yamamoto et al., Agric. Biol. Chem. 55: pp. 1459–1473, 1991.

Yamamoto et al., J. Ferment. Bioeng. 73: pp. 425–430, 1992.

Gavagan et al., J. Org. Chem. 63: pp. 4792–4801, 1998.

Database WP1, Derwent Publications Lts., London, GB; XP002186447, , Nov. 25, 1983.

Database WP1 Section Ch, Derwent Publication Ltd., London, GB; XP002186448 Oct. 20, 1998.

Kobayashi Et Al., "Nitrilase of *Rhodococcus rhodochrous* J1. Purification and Characterization." European Journal of Biochemistry, vol. 182, No. 2, 1989, Pates 349–356, XP001052651.

Amarant Et Al., "Substrates and Inhibitors of the Nitrile Hydratase and Amidase of *Corynebacterium nitrilophilus*", Biotechnology and Applied Biochemistry, vol. 11, No. 1, 1989, pp. 49–59, XP001052649.

(List continued on next page.)

Primary Examiner—Herbert J. Lilling

(57) ABSTRACT

This invention relates to a process for the preparation of a 3-hydroxycarboxylic acid from a 3-hydroxynitrile. More specifically, 3-hydroxyvaleronitrile is converted to 3-hydroxyvaleric acid in high yield at up to 100% conversion, using as an enzyme catalyst 1) nitrile hydratase activity and amidase activity or 2) nitrilase activity of a microbial cell. 3-Hydroxyvaleric acid is used as a substitute for ε-caprolactone in the preparation of highly branched copolyester.

6 Claims, No Drawings

OTHER PUBLICATIONS

Kobayashi Et Al., "Amidase Coupled with Low–Molecular–Mass Nitrile Hydratase from *Rhodococcus rhodochrous* J1", European Journal of Biochemistry, vol. 217, 1993, pp. 327–336, XP000652066.

Kobayashi Et Al., Metalloenzyme Nitrile Hydratase; Structure, Regulation, and Application to Biotechnology, Nature Biotechnology, vol. 16, No. 8, Aug. 1998, PP 733–736, XP002186445.

Pereira Et Al., "A Novel Thermostable Nitrile Hydratase", Extremophiles, vol. 2, Feb. 1998, pp. 347–357, XP002921597.

Gavagan Et Al., "A Gram–Negative Bacterium Producing a Heat–Stable Nitrilase Highly Active on Aliphatic Dinitriles", Applied Microbiology and Biotechnology, vol. 52, Nov. 1999, pp. 654–659, XP000964621.

Yalpani Et Al., Syntheses of Poly(3–Hydroxyalkanoate) (PHA) Conjugates: PHA–Carbohydrate and PHA–Synthetic Polymer Conjugates, Macromolecules, vol. 24, No. 22, Oct. 28, 1991, pp. 6046–6049, XP000258373.

Trollsas Et Al., "Highly Functional Branched and Dendri–Graft Aliphatic Polyesters Through Ring Opening Polymerization", Macromolecules, vol. 31, No. 9, May 5, 1998, pp. 2756–2763, XP002186446.

* cited by examiner

3-HYDROXYCARBOXYLIC ACID PRODUCTION AND USE IN BRANCHED POLYMERS

This application claims benefit to Provisional Ser. No. 60/223,044 filed Aug. 4, 2000.

FIELD OF THE INVENTION

This invention relates to a process for the preparation of a 3-hydroxycarboxylic acid from a 3-hydroxynitrile. More particularly, 3-hydroxyvaleronitrile is converted to 3-hydroxyvaleric acid in high yield at 100% conversion, using as catalyst the nitrile hydratase and amidase activities, or the nitrilase activity, of a microbial cell. 3-Hydroxyvaleric acid is used as a substitute for ε-caprolactone in the preparation of highly branched polyesters.

BACKGROUND OF THE INVENTION

Precise macromolecular engineering is becoming a major trend in polymer technology to satisfy the demand for new properties, improved cost effectiveness, ecology, and quality. Functional polymers with branched, compact structures and terminally located reactive groups are expected to exhibit superior performance/cost characteristics, by virtue of their lower inherent viscosity and higher reactivity versus conventional linear statistical copolymers. Preparation of these polymers can be accomplished by copolymerizing hyperbranching hydroxycarboxylic acid comonomers (hyperbranching $AB_n$ type, where A and B are moieties with hydroxyl- or carboxyl-derived reactive groups, n is 2 or more) (Hult et al., pp. 656–658 and Voit et al., pp. 658–659 in Concise Polymeric Materials Encyclopedia, ed. J. C. Salomone, CRC Press, New York, 1999) and a variety of linear hydroxycarboxylic acid comonomers (linear AB type), including 3-hydroxyvaleric acid.

3-Hydroxyvaleric acid is also useful as a (co)monomer for making linear polyesters. Polyesters are useful as thermoplastic, thermoset, semicrystalline, amphorous, rigid, and elastomeric materials. They are the basis of fibers, films, moldings, and coatings (Goodman, pp. 793–799 in Concise Encyclopedia of Polymer Science and Engineering, ed. J. I. Kroschwitz, John Wiley & Sons, New York, 1990).

3-Hydroxyvaleric acid has been prepared by the β-hydroxylation of valeric acid in fermentation using *Candida rugosa* (Hasegawa et al., *J. Ferment. Technol.* 59: 257–262 (1981); JP 59053838 B4), and a single enantiomer of 3-hydroxyvaleric acid was similarly prepared by fermentative β-hydroxylation of valeric acid with *Pseudomonas putida, Pseudomonas fluorescens, Arthrobacter oxydans* and *Arthrobacter crystallopietes* (U.S. Pat. No. 3,553,081). These methods for fermentative oxidation of valeric acid typically produce 3-hydroxyvaleric acid at low product concentrations, and require an elaborate and expensive separation of 3-hydroxyvaleric acid from the fermentation broth. (R)-(−)-3-Hydroxyvaleric acid has been prepared by the chemical degradation (Seebach et al., *Helv. Chim. Acta* 77:2007–2034 (1994)) or by fermentative autodegradation (WO 9929889) of poly(3-hydroxybutyrate/3-hydroxyvalerate), but degradation of hydroxybutyric acid/hydroxyvaleric acid copolymers also requires a difficult separation of 3-hydroxybutyric acid from the co-product 3-hydroxyvaleric acid. (R)-(−)-3-Hydroxyvaleric acid has also been prepared by the enzymatic reduction of 3-oxovaleric acid (Bayer et al., *Appl. Microbiol. Biotechnol.* 42:543–547 (1994)) or by the asymmetric hydrogenation of methyl 3-oxovalerate followed by saponification (Burk et al., *Organometallics* 9:2653–2655 (1990)).

Nitriles are readily converted to the corresponding carboxylic acids by a variety of chemical processes. These processes typically require strongly acidic or basic reaction conditions and high reaction temperatures, and usually produce unwanted byproducts and/or large amounts of inorganic salts as unwanted waste. Reaction conditions for the chemical hydrolysis of nitriles which additionally have a hydroxyl group, such as for the conversion of 3-hydroxyvaleronitrile to 3-hydroxyvaleric acid, will usually also result in the undesirable elimination of primary, secondary, or tertiary hydroxyl groups to produce carbon—carbon double bonds.

The enzyme-catalyzed hydrolysis of nitriles substrates to the corresponding carboxylic acids is often preferred to chemical methods, since the reactions are often run at ambient temperature, do not require the use of strongly acidic or basic reaction conditions, and produce the desired product with high selectivity at high conversion.

A combination of two enzymes, nitrile hydratase and amidase, can be used to convert aliphatic nitrites to the corresponding carboxylic acid in aqueous solution. The aliphatic nitrile is initially converted to an amide by the nitrile hydratase, then the amide is subsequently converted by the amidase to the corresponding carboxylic acid. A wide variety of bacterial genera are known to possess a diverse spectrum of nitrile hydratase and amidase activities (Sugai et al., *Biosci. Biotech. Biochem.* 61:1419–1427 (1997)), including Rhodococcus, Pseudomonas, Alcaligenes, Arthrobacter, Bacillus, Bacteridium, Brevibacterium, Corynebacterium and Micrococcus. The fungus *Fusarium merismoides* TG-1 has also been used as catalyst for the hydrolysis of aliphatic nitrites and dinitriles (Asano et al., *Agric. Biol. Chem.* 44:2497–2498 (1980)). Immobilized nitrile hydratase and amidase from Rhodococcus sp. (SP409 from Novo Industri) was used to hydrolyze 3-hydroxypropionitrile, 3-hydroxyheptanenitrile, 3-hydroxyoctanenitrile, and 3-hydroxynonanenitrile to the corresponding 3-hydroxycarboxylic acids in 63%, 62% and 83% yields, respectively (de Raadt et al., *J. Chem. Soc. Perkin Trans.* 1, 137–140 (1992)). The formation of the corresponding amide was also observed by TLC. In contrast, the purified nitrile hydratase of *Bacillus pallidus* Dac521 hydrolyzed a variety of aliphatic nitrites, but did not hydrolyze 3-hydroxypropionitrile (Cramp et al., *Biochim. Biophys. Acta* 1431:249–260 (1999)).

A single enzyme, nitrilase, also converts a nitrile to the corresponding carboxylic acid and ammonia in aqueous solution, but without the intermediate formation of an amide. Kobayashi et al. (*Tetrahedron* 46:5587–5590 (1990); *J. Bacteriology* 172:4807–4815 (1990)) have described an aliphatic nitrilase isolated from *Rhodococcus rhodochrous* K22 which catalyzed the hydrolysis of a variety of aliphatic nitrites to the corresponding carboxylic acids. A nitrilase from *Comamonas testosteroni* has been isolated that can convert a range of aliphatic α,ω-dinitriles to either the corresponding ω-cyanocarboxylic acids or dicarboxylic acids (CA 2,103,616; Lévy-Schil et al., *Gene* 161:15–20 (1995)). Aliphatic nitrilases are also produced by *Rhodococcus rhodochrous* NIMBI 11216 (Bengis-Garber et al., *Appl. Microbiol. Biotechnol.* 32:11–16 (1989); Gradley et al., *Biotechnology Lett.* 16:41–46 (1994)), *Rhodococcus rhodochrous* PA-34 (Bhalla et al., *Appl. Microbiol. Biotechnol.* 37:184–190 (1992)), *Fusarium oxysporum* f. sp. *melonis* (Goldlust et al., *Biotechnol. Appl. Biochem.* 11:581–601 (1989)), *Acinetobacter* sp. AK 226 (Yamamoto et al., *Agric. Biol. Chem.* 55:1459–1473 (1991)), *Alcaligenes faecalis* ATCC 8750 (Yamamoto et al., *J. Ferment. Bioeng.*

73:425–430 (1992)), and *Acidovorax facilis* 72W (Gavagan et al., *J. Org. Chem.* 63:4792–4801 (1998)).

The problem to be solved, therefore, is to provide new catalysts useful for converting nitriles to their corresponding carboxylic acids at high yield. More specifically, the ability to convert a nitrile functional group in a compound to the corresponding carboxylic acid in the presence of a hydroxyl group that can undergo elimination would be extremely useful.

SUMMARY OF THE INVENTION

A process is disclosed for hydrolyzing 3-hydroxynitrile to 3-hydroxycarboxylic acid. The process includes the steps of (a) contacting a 3-hydroxynitrile in an aqueous reaction mixture with an enzyme catalyst characterized by 1) nitrile hydratase and amidase activity or 2) nitrilase activity; and (b) optionally, recovering the 3-hydroxycarboxylic acid produced in step (a). More particularly, 3-hydroxyvaleronitrile is converted in the invention to 3-hydroxyvaleric acid in high yield at up to 100% conversion, using as an enzyme catalyst 1) nitrile hydratase activity and amidase activity or 2) nitrilase activity of a microbial cell.

Further embodiments of the invention to hydrolyze 3-hydroxynitrile to 3-hydroxycarboxylic acid use an enzyme catalyst having 1) nitrile hydratase activity and amidase activity or 2) nitrilase in the form of whole microbial cells, permeabilized microbial cells, one or more cell components of a microbial cell extract, partially-purified enzyme(s), or purified enzyme(s). Preferably, the form of enzyme catalyst is whole microbial cells, or (for the embodiment of the process using nitrile hydratase and amidase activity) an additional preferred form of enzyme catalyst is as partially purified or purified enzyme. These different forms of enzyme catalyst can be immobilized on or in a soluble or insoluble support. Microorganisms characterized by nitrile hydratase activity and amidase activity and useful in the process are *Acidovorax facilis* 72W (ATCC 55746), *Comamonas testosteroni* 22-1(ATCC PTA-1853), *Comamonas testosteroni* 5-MGAM-4D (ATCC 55744), *Dietzia sp.* ADL1 (ATCC PTA-1854), *Syctalidium spp.* 3LD-122P (ATCC PTA-1855), *Rhodococcus sp.* 25-1 (ATCC PTA-1856), and *Pseudomonas putida* 5B-MGN-2P (NRRL-B-18668). Microorganisms characterized by a nitrilase activity and useful in the process are *Acidovorax facilis* 72W (ATCC 55746) (after heating at 50° C. for 0.5–1 hour to inactivate undesirable nitrile hydratase and amidase activities), *Acidovorax facilis* 72-PF-17 (ATCC 55745) and *Acidovorax facilis* 72-PF-15 (ATCC 55747).

The invention is useful in producing a highly branched copolyester comprising at least two repeat units derived from at least one linear 3-hydroxycarboxylic acid or its ester of the structure $R^2O-CR^4R^5CR^6R^7C(O)OR^1$ and at least one hyperbranching hydroxycarboxylic acid or its ester of the structure $(R^2O)_n\text{-}R\text{-}[C(O)OR^1]_m$, wherein R is $C_{1-12}$ hydrocarbyl radical with n+m free valencies, $R^1$ is H, $C_{1-12}$ or hydroxyl substituted $C_{1-12}$ hydrocarbyl radical, $R^3$, $R^4$, $R^5$, $R^6$, $R^7$ is H or $C_{1-12}$ hydrocarbyl radical, $R^2$ is H or $(O)CR^3$, n+m is 3 or more, and provided that one of n and m is 1.

Additionally, the invention includes a process for synthesizing a highly branched copolyester product comprising the steps of: (a) contacting and heating a mixture of (1) at least one hyperbranching hydroxycarboxylic acid or its ester of the structure $(R^2O)_n\text{-}R\text{-}[C(O)O\ R^1]_m$, wherein R is $C_{1-12}$ hydrocarbyl radical with n+m free valencies, $R^1$ is H, $C_{1-12}$ or hydroxyl substituted $C_{1-12}$ hydrocarbyl radical, $R^3$, $R^4$, $R^5$, $R^6$, $R^7$ is H or $C_{1-12}$ hydrocarbyl radical, $R^2$ is H or $(O)CR^3$, n+m is 3 or more, and provided that one of n and m is 1, (2) a linear 3-hydroxycarboxylic acid or its ester of the structure $R^2O-CR^4R^5CR^6R^7C(O)OR^1$, and (3) an esterification catalyst; and (b) collecting the highly branched copolyester product of step (a). In this process, the hyperbranching hydroxycarboxylic acid is preferably dimethylolpropionic acid or trimethylolacetic acid, the linear hydroxycarboxylic acid is preferably 3-hydroxyvaleric acid. Examples of the linear 3-hydroxycarboxylic acids include but are not limited to the following compounds: 3-hydroxypropionic acid, 3-hydroxybutyric acid, 3-hydroxypentanoic acid, 3-hydroxyhexanoic acid, 3-hydroxy-3-isopropyl-4-methylpentanoic acid, 3-hydroxy-3-phenylpropanoic acid, 2-propyl-3-hydroxypentanoic acid, 3-hydroxy-3-methyl-n-valeric acid, and 3-hydroxy-2,2-dimethylpropionic acid. The esterification catalyst may be any conventionally known such as a protonic acid, Lewis acid, or a basic catalyst including sulfonic acids, phosphoric and phosphonic acids, titanium alkoxides, dialkyltin oxide, oxides, carbonates and carboxylates of tin, zinc, manganese, calcium, magnesium, or antimony. The esterification catalyst is preferably tin dicarboxylate or a protonic acid.

An additional embodiment of the invention uses a linear 3-hydroxycarboxylic acid produced with an enzyme catalyst as described herein to synthesize a highly branched copolyester product. The enzymatically-produced linear 3-hydroxycarboxylic acid is heated in contact with at least one hyperbranched hydroxycarboxylic acid or its ester as discussed herein, and an esterification catalyst.

BRIEF DESCRIPTION OF THE BIOLOGICAL DEPOSITS

Applicants have made the following biological deposits under the terms of the Budapest Treaty:

| Depositor Identification Reference | Int'l. Depository Designation No. | Date of Deposit |
| --- | --- | --- |
| *Acidovorax facilis* 72-PF-17 | ATCC 55745 | 8 Mar. 1996 |
| *Acidovorax facilis* 72W | ATCC 55746 | 8 Mar. 1996 |
| *Acidovorax facilis* 72-PF-15 | ATCC 55747 | 8 Mar. 1996 |
| *Comamonas testosteroni* 22-1 | ATCC PTA-1853 | 10 May 2000 |
| *Comamonas testosteroni* 5-MGAM-4D | ATCC 55744 | 8 Mar. 1996 |
| *Dietzia* sp. ADL1 | ATCC PTA-1854 | 10 May 2000 |
| *Scytalidium* spp. 3LD-122P | ATCC PTA-1855 | 10 May 2000 |
| *Rhodococcus* sp. 25-1 | ATCC PTA-1856 | 10 May 2000 |
| *Pseudomonas putida* 5B-MGN-2P | NRRL-B-18668 | 6 Jul. 1990 |

As used herein, "ATCC" refers to the American Type Culture Collection international depository located at 10801 University Boulevard, Manassas, Va. 20110-2209 U.S.A. As used herein, "NRRL" refers to the Agricultural Research Service Culture Collection, part of the Microbial Properties Research Unit located at the National Center for Agricultural Utilization Research, 1815 North University Street, Peoria, Ill. 61604, U.S.A. The "Int'l Depository Designation No." is the accession number to cultures on deposit with the ATCC or the NRRL, respectively.

The listed deposit(s) will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

Applicants have solved the stated problem by using an enzyme catalyst to convert the nitrile functional group of a 3-hydroxynitrile to its corresponding carboxylic acid in the presence of a hydroxyl group that can undergo elimination. This process offers significant advantages in the preparation of, for example, 3-hydroxyvaleric acid or 3-hydroxypropionic acid over other chemical or enzymatic methods of nitrile hydrolysis, and makes possible the preparation of 3-hydroxycarboxylic acids such as 3-hydroxyvaleric acid or 3-hydroxypropionic acid in high yield from relatively inexpensive and readily prepared starting materials, with very little byproduct and waste production.

The invention relates to the production of improved polyesters for use primarily in coatings, but also in fibers, films, and moldings. Material of the invention also has utility as a crosslinker. The 3-hydroxyvaleric acid produced by the present invention is useful as an ingredient in the preparation particularly of highly branched polyesters in combination with the hyperbranching hydroxycarboxylic comonomer and is useful as a (co)monomer in biodegradable polyester production.

Specifically, a process to prepare 3-hydroxyvaleric acid from 3-hydroxyvaleronitrile in high yields has been demonstrated that uses 1) nitrilase activity, or 2) nitrile hydratase activity and amidase activity of microbial cells. A nitrilase enzyme directly converts an aliphatic or aromatic nitrile to the corresponding carboxylic acid, without the formation of the corresponding amide intermediate (Equation 1), whereas nitrile hydratase (NHase) initially converts an aliphatic or aromatic nitrile to an amide, and then the amide is subsequently converted by the amidase to the corresponding carboxylic acid (Equation 2):

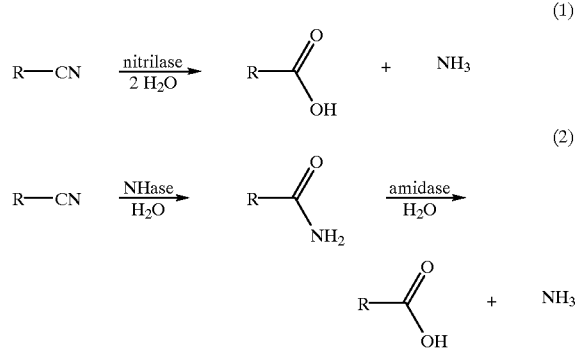

Similar yields of 3-hydroxyvaleric acid have been obtained using purified enzyme(s), cell extracts, microbial cells and immobilized microbial cells, as described in the accompanying Examples.

Several classes of highly branched copolyester polyols have been prepared using dimethylolpropionic acid as a branching comonomer and a variety of linear hydroxycarboxylic acids and lactones. Some of these polymers demonstrate attractive characteristics. The corresponding block copolymers with similar overall composition but of different microstructure have been reported (e.g., DMPA/ε-caprolactone block copolymers described in *Macromolecules*, 30: 8508 (1997) and *J. Polym. Sci. Part (A): Polymer Chemistry* 36: 2793 (1998)). Highly branched copolyester polyol substrates for reactive coatings with desirable, significantly enhanced $T_g$ have now been obtained with the present invention when 3-hydroxycarboxylic acids such as 3-hydroxyvaleric acid or 3-hydroxy-2,2-dimethylpropionic acid were substituted for ε-caprolactone as a linear comonomer in the copolymerization with dimethylolpropionic acid or trimethylolacetic acid. The higher $T_g$ signficantly expands the range of applications to which branched copolyesters can be put.

The claimed invention for preparing 3-hydroxycarboxylic acids generates little waste or reaction byproducts, and the 3-hydroxycarboxylic acid is readily recovered from the product mixture. Previously known chemical methods for the hydrolysis of 3-hydroxynitriles cannot produce the high yields and selectivities to 3-hydroxycarboxylic acids obtained using enzyme-catalyzed nitrile hydrolysis. Non-enzymatic nitrile hydrolysis reactions typically involve heating solutions of the nitrile at elevated temperatures, often times in the presence of strong acid or base, while the enzyme-catalyzed reactions described above are carried out at ambient temperature in aqueous solution and at neutral pH with no added acid or base. For example, aqueous barium hydroxide has been used to hydrolyze 3-aminopropionitrile to 3-alanine in 85 to 90% yield (Ford, *Org. Synth.*, Coll. vol. III: 34–36 (1955)), and 3-cyanobutyric acid to methylsuccinic acid in 72% yield (Brown, *Org Synth.*, Coll. vol. III: 615–617 (1955)); repeating the first of these two procedures with 3-hydroxyvaleronitrile produced little or no detectable 3-hydroxyvaleric acid (see Comparative Example).

In this disclosure, a number of terms and abbreviations are used. The following definitions are provided.

"Nitrile hydratase" is abbreviated NHase.

"Nitrile hydratase-deficient" describes cells that have no nitrile hydratase activity as a result of heat treatment.

"Enzyme catalyst" refers to a catalyst which is characterized by 1) nitrilase activity or 2) nitrile hydratase activity and amidase activity. The enzyme catalyst may be in the form of a whole microbial cell, permeabilized microbial cell(s), one or more cell components of a microbial cell extract, partially purified enzyme, or purified enzyme.

A saturated "hydrocarbyl radical" is defined as any radical composed exclusively of carbon and hydrogen, where single bonds are exclusively used to join carbon atoms together. Thus, any stable arrangement of carbon and hydrogen atoms, having at least one carbon atom, is included within the scope of a saturated hydrocarbon radical.

The terms "hyperbranched", "highly branched", and "dendritic macromolecules" (dendrimers) can generally be described as three-dimensional, highly branched molecules having a tree-like structure. Dendrimers are highly symmetrical, while similar macromolecules designated as hyperbranched or highly branched may to a certain degree hold an asymmetry, yet maintain the highly branched tree-like structure. Dendrimers can be said to be monodisperse variations of hyperbranched macromolecules. Hyperbranched, highly branched, and dendritic macromolecules normally consist of an initiator or nucleus having one or more reactive sites and a number of surrounding branching layers and, optionally, a layer of chain terminating molecules. The layers are usually called generations.

"3-Hydroxynitrile" is equivalent to "β-Hydroxynitrile". 3-Hydroxynitriles include but are not limited to the following compounds: 3-hydroxypropionitrile, 3-hydroxybutyronitrile, 3-hydroxyvaleronitrile, 3-hydroxyhexanenitrile, 3-hydroxyheptanenitrile, 3-hydroxyoctanenitrile, 3-hydroxynonanenitrile, 3-hydroxy-3-isopropyl-4-methylpentanenitrile, 3-hydroxy-3-phenylpropanenitrile, 2-propyl-3-hydroxypentanenitrile and 3-hydroxy-3-methyl-n-pentanenitrile.

"3-Hydroxycarboxylic acid" is equivalent to "β-Hydroxycarboxylic acid". 3-Hydroxycarboxylic acids include but are not limited to the following compounds: 3-hydroxypropionic acid, 3-hydroxybutyric acid, 3-hydroxypentanoic acid, 3-hydroxyhexanoic acid, 3-hydroxy-3-isopropyl-4-methylpentanoic acid, 3-hydroxy-3-phenylpropanoic acid, 2-propyl-3-hydroxypentanoic acid, 3-hydroxy-2,2-dimethylpropionic acid, and 3-hydroxy-3-methyl-n-valeric acid.

"3-Hydroxyvaleronitrile" is also known as 3-hydroxypentanenitrile and β-hydroxyvaleronitrile.

"3-Hydroxyvaleric acid" is also known as 3-hydroxypentanoic acid and β-hydroxyvaleric acid.

"3-Hydroxypropionitrile" is also known as hydracrylonitrile, 3-cyanoethanol, 3-hydroxyethyl cyanide, 3-hydroxypropionitrile, 1-cyano-2-hydroxyethane, 2-cyanoethanol, 2-cyanoethyl alcohol, 2-hydroxycyanoethane, 2-hydroxyethyl cyanide, 3-hydroxypropanenitrile, 3-hydroxypropionitrile, ethylene cyanohydrin, glycol cyanohydrin.

"3-Hydroxypropionic acid" is also known as hydracrylic acid, β-hydroxypropionic acid, 3-lactic acid, 2-deoxyglyceric acid, 3-hydroyxpropanoic acid, and ethylenelactic acid.

"Dimethylolpropionic acid" is also known as 2,2-bis(hydroxymethyl)-propionic acid and α,α-bis(hydroxymethyl)propionic acid.

"Trimethylolacetic acid" is also known as 3-hydroxy-2,2-bis(hydropoxymethyl)-propanoic acid, 2,2-bis(hydroxymethyl)-hydracrylic acid, 2-carboxy-2-(hydroxymethyl)-1,3-propanediol; 3-hydroxy-2,2-bis(hydroxymethyl)Propionic acid; 3-hydroxy-2,2 -dihydroxymethylpropionic acid; tris(hydroxymethyl)acetic acid.

The terms "protic acid" and "protonic acid" refer to acids having an ionizable proton (i.e., capable of acting as a proton donor) strongly or weakly acidic. These acids include, but are not limited to, aromatic or aliphatic carboxylic acids, aromatic or aliphatic sulfonic acids, phosphoric acid, sulfuric acid, sulfurous acid, nitric acid, perchloric acid, hydrochloric acid, and the like (often referred to as Lowry-Brønsted acids). Examples of non-protonic acids (i.e., acids that can accept an electron pair to form a covalent bond) are Lewis acids such as boron trifluoride, aluminum trichloride, and stannic chloride.

DESCRIPTION OF THE PREFERRED EMBODIMENTS

Growth of Microbial Enzyme Catalysts:

Microbial strains used for conversion of 3-hydroxynitriles were isolated as described below. Frozen 15% glycerol stocks were maintained at −65° C. to −70° C.

Rhodococcus sp. 25-1 Comamonas testosteroni 22-1, Acidovorax facilis 72W, and Comamonas testosteroni 5-MGAM-4D were enriched from soil collected in Orange, Tex., U.S.A., using standard enrichment procedures with E2 basal medium (Table 1) (pH 7.2).

TABLE 1

| E2 Basal Medium g/L | | | |
|---|---|---|---|
| $KH_2PO_4$ | 1.4 | $NaMoO_4.2H_2O$ | 0.0025 |
| $NaH_2PO_4$ | 6.9 | $NiCl_2.6H_2O$ | 0.01 |
| KCl | 0.5 | $CuSO_4.2H_2O$ | 0.005 |
| $MgSO_4.7H_2O$ | 0.5 | biotin | 0.0002 |
| $CaCl_2$ | 0.025 | folic acid | 0.0002 |

TABLE 1-continued

| E2 Basal Medium g/L | | | |
|---|---|---|---|
| NaCl | 1 | pyridoxine · HCl | 0.001 |
| sodium citrate | 0.1 | riboflavine | 0.0005 |
| $FeSO_4.7H_2O$ | 0.05 | nicotinic acid | 0.0005 |
| $CoCl_2.6H_2O$ | 0.01 | pantothenic acid | 0.0005 |
| $MnCl_2.4H_2O$ | 0.001 | Vitamin B12 | 0.00001 |
| $ZnCl_2$ | 0.0005 | p-aminobenzoic acid | 0.0005 |
| $H_3BO_3$ | 0.000062 | | |

Table 2 contains modifications that were made to the E2 basal medium for the enrichments described above.

TABLE 2

| Strain | Enrichment Nitrile | Other |
|---|---|---|
| Rhodococcus sp. 25-1 | 0.2% 3-hydroxyvaleronitrile | 0.6% glycerol |
| Comamonas testosteroni 22-1 | 0.2% 3-hydroxyvaleronitrile | 0.6% glycerol |
| Acidovorax facilis 72W | 0.2% ethylsuccinonitrile | 0.6% glycerol |
| Comamonas testosteroni 5-MGAM-4D | 1% methylglutaramide | 0.6% glycol |

"Comamonas testosteroni 5-MGAM-4D 1% methylglutaramide 0.6% glycol"

Scytalidium spp. 3LD-122P and Pseudomonas putida 5B-MGN-2P were enriched from soil collected in Orange, Tex., U.S.A., using standard enrichment procedures with PR basal medium (Table 3) (pH 7.2).

TABLE 3

| PR Basal Medium g/L | | | |
|---|---|---|---|
| $KH_2PO_4$ | 8.85 | $NiCl_2.6H_2O$ | 0.000024 |
| sodium citrate | 0.225 | $CuCl_2.2H_2O$ | 0.000017 |
| $MgSO_4.7H_2O$ | 0.5 | biotin | 0.00001 |
| $FeSO_4.7H_2O$ | 0.05 | folic acid | 0.00005 |
| $FeCl_2.4H_2O$ | 0.0015 | pyridoxine.HCl | 0.000025 |
| $CoCl_2.6H_2O$ | 0.0002 | riboflavin | 0.000025 |
| $MnCl_2.4H_2O$ | 0.0001 | nicotinic acid | 0.000025 |
| $ZnCl_2$ | 0.00007 | pantothenic acid | 0.00025 |
| $H_3BO_3$ | 0.000062 | Vitamin $B_{12}$ | 0.000007 |
| $NaMoO_4.2H_2O$ | 0.000036 | p-aminobenzoic acid | 0.00025 |

Table 4 contains modifications that were made to the PR basal medium for the enrichments described above.

TABLE 4

| Strain | Enrichment Nitrile, 25 mM | Other |
|---|---|---|
| Scytalidium spp. 3LD-122P | 2-methylglutaronitrile | 30 g/L glucose, pH 5.6 |
| Pseudomonas putida 5B-MGN-2P | 2-methylglutaronitrile | 3 g/L $Na_2$succinate · $2H_2O$ |

Dietzia sp. ADL1 was isolated from an enrichment culture. The enrichment culture was established by inoculating 1 mL of sludge into 10 mL of S12-N medium in a 50 mL screw cap Erlenmeyer flask. S12-N medium contains the following: $Na_2SO_4$, 10 mM; potassium phosphate buffer, pH 7.0, 50 mM; $MgCl_2$, 2 mM; $CaCl_2$, 0.7 mM; $MnCl_2$, 50 μM; $FeCl_3$, 1 μM; $ZnCl_3$, 1 μM; $CuSO_4$, 1.72 μM; $CoCl_2$, 2.53 μM; $Na_2MoO_2$, 2.42 μM; $FeSO_4$, 0.0001%; yeast extract, 0.001%; and thiamine hydrochloride, 2 μM. The sludge was obtained from a waste water treatment testing system used by E. I. du Pont de Nemours and Company in Victoria, Tex. The enrichment culture was supplemented with 100 ppm adiponitrile added directly to the culture medium and was incubated at 30° C. with reciprocal shaking. The enrichment culture was maintained by adding 100 ppm of toluene every 2–3 days. The culture was diluted every 10 days by replacing 9 mL of the culture with the same volume of S12-N medium. Bacteria that utilize adiponitrile as a sole source of carbon, nitrogen, and energy were isolated by spreading samples of the enrichment culture onto S12-N agar (S12-N medium with 1.5% Difco Noble Agar). Adiponitrile (10 µL) was placed on the interior of each Petri dish lid. The Petri dishes were sealed with parafilm and incubated upside down at 28° C. Representative bacterial colonies were then single colony passaged several times on S12-N agar with adiponitrile supplied on the interior of each Petri dish lid. The Petri dishes were sealed with parafilm and incubated upside down at 28° C. Dietzia sp. ADL1 was one of the several strains isolated.

The various strains were grown aerobically under the following conditions (Tables 5 and 6) for testing nitrile transformation activity.

TABLE 5

| Strain | Nitrile/ Amide | Medium | °C. | Time, h |
|---|---|---|---|---|
| 5B-MGN-2P | none | Lauria Broth + 0.5% (w/v) Na$_2$succinate.2H$_2$O | 32 | 24 |
| 3LD-122P | 0.2% (v/v) 3-hydroxy-valeronitrile | E2, 1.0% (w/v) glucose | 32 | 48 |
| 22-1 | 0.1% (v/v) butyronitrile | E2, 1% (w/v) glucose | 30 | 28 |
| 25-1 | 0.2% (v/v) butyronitrile | E2, 0.6% (v/v) glycerol | 30 | 48 |
| 5-MGAM-4D | 0.2% (w/v) propionamide | E2, 0.6% (w/v) glucose + Na$_2$succinate.2H$_2$O | 30 | 29 |
| ADL1 | 0.2% (v/v) adiponitrile | E2, 0.6% (v/v) glycerol | 30 | 48 |

Additionally, *Acidovorax facilis* 72W was grown aerobically. At inoculation, the fermenter contained 8.5 L of Fermenter Medium (Table 6) plus 218 g of Nutrient Feed solution (see below), giving a starting concentration of approximately 7 g/L glycerol. Dissolved oxygen was held at 25% of saturation, at 32° C., and pH at 6.8–7.0. At 18 h post inoculation, feeding of Nutrient Feed solution began. The Nutrient Feed solution included the following components which were sterilized separately and combined after cooling: potassium phosphate, monobasic, 19.6 g in 0.25 L deionized water; magnesium sulfate, heptahydrate, 3.3 g plus sulfuric acid, 4 mL, in 0.15 L deionized water; Trace Metal (Table 6) solution, 67 mL, plus 400 g glycerol in 0.80 L deionized water. Initially, the Nutrient Feed solution was added at a rate of 0.4 g feed/minute (0.15 g glycerol/min). At 26 h, the feed rate was increased to 0.9 g feed/min (0.3 g glycerol/min). A final increase in feed rate to 1.8 g feed/min (0.6 g glycerol/min) was made at 34 h. 72W Cells were harvested at 58 hours.

TABLE 6

| Component | Stock Concentration | Component | Stock Concentration |
|---|---|---|---|
| Fermenter Medium: | | | |
| potassium phosphate, monobasic | 0.39 g/L | potassium phosphate, dibasic | 0.39 g/L |
| Difco yeast extract | 5.0 g/L | | |

TABLE 6-continued

| Component | Stock Concentration | Component | Stock Concentration |
|---|---|---|---|
| Trace Metal Solution: | | | |
| hydrochloric acid | 10 mL/L | zinc sulfate, heptahydrate | 1.77 g/L |
| calcium chloride, dihydrate | 11.4 g/L | sodium molybdate, dihydrate | 0.05 g/L |
| manganese sulfate, monohydrate | 1.23 g/L | vanadyl sulfate, dihydrate | 0.08 g/L |
| copper sulfate, pentahydrate | 0.63 g/L | nickel nitrate, hexahydrate | 0.04 g/L |
| cobalt chloride, hexahydrate | 0.16 g/L | sodium selenite | 0.04 g/L |
| boric acid | 0.91 g/L | ferrous fulate, heptahydrate | 6.0 g/L |

Harvested cells were frozen at −65 to −70° C. until used for nitrile transformation. For use as an enzyme catalyst having only nitrilase activity, a 10 to 50% (wet cell weight) suspension of *Acidovorax facilis* 72W cells in 0.35 M phosphate buffer (pH 7.0) were first heated to 50° C. for 1 h to inactivate the nitrile hydratase and amidase enzymes present without measurably decreasing the nitrilase activity. *Acidovorax facilis* 72W cells which were not heat-treated at 50° C., and which had nitrilase, and nitrile hydratase and amidase activities produced yields of 3-hydroxyvaleric acid similar to heat-treated, nitrilase-only containing cells.

Two mutants of the *Acidovorax facilis* 72W (ATCC 55746) strain have been prepared (U.S. Pat. No. 5,858,736, incorporated by reference) which produce only very low levels of the undesirable nitrile hydratase activity responsible for non-regioselective nitrile hydrolysis of aliphatic dinitriles. These nitrile hydratase-deficient mutant strains, *Acidovorax facilis* 72-PF-15 (ATCC 55747) and *Acidovorax facilis* 72-PF-17 (ATCC 55745), do not require heat-treatment of the cells prior to use as an enzyme catalyst for the hydrolysis of 3-hydroxyvaleronitrile to 3-hydroxyvaleric acid. In cases where the regioselectivity of the nitrilase is not required, the *Acidovorax facilis* 72W (ATCC 55746) strain does not have to be heat-treated in order to deactivate the non-regioselective nitrile hydratase activity.

Preparation of Cell Extract:

All steps in this procedure were performed at 5° C. and at pH 7.5. A 25 wt % suspension of *Comamonas testosteroni* 22-1 (ATCC PTA-1853) wet cell paste was prepared in 100 mM potassium phosphate buffer (pH 7.0), 0.1 mM phenyl methyl sulfonyl fluoride (PMSF) and 2.0 mM dithiothreitol. An extract of this suspension was prepared by passage through a French press (American Instrument Co., Silver Springs, Md., U.S.A.) according to methods known to the art. The cell extract was prepared by a centrifugation at 27,500 g for 30 minutes to remove cell debris.

Preparation of 3-Hydroxyvaleronitrile:

3-Hydroxyvaleronitrile has been prepared by reacting hydrogen cyanide with 1,2-epoxybutane in the presence of triethylaluminum (FR 1446127), and by the reaction of acetonitrile and propionaldehyde in the presence of di-n-butylboryl triflate (Hamana et al., *Chem. Lett.* 1401–1404 (1982)). Optically active 3-hydroxyvaleronitrile has been prepared by the lipase-catalyzed hydrolysis of 2-cyano-1-methylethyl acetate (Itoh et al., *J. Org. Chem.* 62:9165–9172 (1997)).

Hydrolysis of 3-Hydroxynitrile to 3-Hydroxycarboxylic Acid:

The hydrolysis reaction is performed by mixing a 3-hydroxynitrile, for example, 3-hydroxyvaleronitrile, with an aqueous suspension of the appropriate enzyme catalyst. Whole microbial cells can be used as an enzyme catalyst without any pretreatment. Alternatively, they can be immobilized in a polymer matrix (e.g., alginate beads or polyacrylamide gel (PAG) particles) or on an insoluble solid support (e.g., celite) to facilitate recovery and reuse of the enzyme catalyst. The enzyme(s) can also be isolated from the whole cells and used directly as a catalyst, or the enzyme(s) can be immobilized in a polymer matrix or on an insoluble support. Methods for the immobilization of cells, or the isolated enzymes, have been widely reported and are well known to those skilled in the art (Methods in Biotechnology, Vol. 1: Immobilization of Enzymes and Cells; Gordon F. Bickerstaff, Editor; Humana Press, Totowa, N.J., USA; 1997).

The concentration of enzyme catalyst in the aqueous reaction mixture depends on the specific catalytic activity of the enzyme catalyst and is chosen to obtain the desired rate of reaction. The wet cell weight of the microbial cells used as catalyst in hydrolysis reactions typically ranges from 0.001 grams to 0.100 grams of wet cells per mL of total reaction volume, preferably from 0.002 grams to 0.050 grams of wet cells per mL. The specific activity of the microbial cells (IU/gram wet cell wt.) is determined by measuring the rate of conversion of a 0.10 M solution of 3-hydroxyaleronitrile to 3-hydroxyvaleric acid at 25° C., using a known weight of microbial cell catalyst. An IU (International Unit) of enzyme activity is defined as the amount of enzyme activity required to convert one micromole of substrate to product per minute.

The temperature of the hydrolysis reaction is chosen to optimize both the reaction rate and the stability of the enzyme catalyst activity. The temperature of the reaction may range from just above the freezing point of the suspension (approximately 0° C.) to 65° C., with a preferred range of reaction temperature of from 5° C. to 35° C. The microbial cell catalyst suspension may be prepared by suspending the cells in distilled water, or in a aqueous solution of a buffer which will maintain the initial pH of the reaction between 5.0 and 10.0, preferably between 6.0 and 9.0. As the reaction proceeds, the pH of the reaction mixture may change due to the formation of an ammonium salt of the carboxylic acid from the corresponding nitrile functionality. The reaction can be run to complete conversion of 3-hydroxynitrile with no pH control, or a suitable acid or base can be added over the course of the reaction to maintain the desired pH.

3-Hydroxyvaleronitrile was found to be completely miscible with water in all proportions at 25° C. In cases where reaction conditions are chosen such that the solubility of 3-hydroxyvaleronitrile is also dependent on the temperature of the solution and/or the salt concentration (buffer or product 3-hydroxyvaleric acid ammonium salt) in the aqueous phase, the reaction mixture may initially be composed of two phases: an aqueous phase containing the enzyme catalyst and dissolved 3-hydroxyvaleronitrile, and an organic phase (the undissolved 3-hydroxyvaleronitrile). As the reaction progresses, the 3-hydroxyvaleronitrile dissolves into the aqueous phase, and eventually a single phase product mixture is obtained. The reaction may also be run by adding the 3-hydroxyvaleronitrile to the reaction mixture at a rate approximately equal to the enzymatic hydrolysis reaction rate, thereby maintaining a single-phase aqueous reaction mixture, and avoiding the potential problem of substrate inhibition of the enzyme at high starting material concentrations.

3-Hydroxyvaleric acid may exist in the product mixture as a mixture of the protonated carboxylic acid and its corresponding ammonium salt (dependent on the pH of the product mixture), and may additionally be present as a salt of the carboxylic acid with any buffer which may additionally be present in the product mixture. The 3-hydroxyvaleric acid product may be isolated from the reaction mixture as the protonated carboxylic acid, or as a salt of the carboxylic acid, as desired.

The final concentration of 3-hydroxyvaleric acid in the product mixture at complete conversion of 3-hydroxyvaleronitrile may range from 0.001 M to the solubility limit of the 3-hydroxyvaleric acid product. Preferably, the concentration of 3-hydroxyvaleric acid will range from 0.10 M to 2.0 M. 3-Hydroxyvaleric acid may be isolated from the product mixture (after removal of the catalyst) by adjusting the pH of the reaction mixture to between 1.0 and 2.5 with concentrated hydrochloric acid, saturation of the resulting solution with sodium chloride, and extraction of 3-hydroxyvaleric acid with a suitable organic solvent such as methyl t-butyl ether, ethyl ether, or dichloromethane. The combined organic extracts are then combined, stirred with a suitable drying agent (e.g., magnesium sulfate), filtered, and the solvent removed (e.g., by rotary evaporation) to produce the desired product in high yield and in high purity (typically 98–99% pure). If desired, the product can be further purified by recrystallization or distillation.

The enzymatic hydrolysis of 3-hydroxypropionitrile to 3-hydroxypropionic acid was performed using methods similar to those described above for 3-hydroxyvaleronitrile (see accompanying Examples), and produced 3-hydroxypropionic acid in 99% to 100% yields at complete conversion of 3-hydroxypropionitrile. Additional 3-hydroxynitriles which may be converted by the present methods to the corresponding 3-hydroxycarboxylic acids include, but are not limited to, 3-hydroxybutyronitrile, 3-hydroxyhexanenitrile, 3-hydroxyheptanenitrile, 3-hydroxyoctanenitrile, 3-hydroxynonanenitrile, 3-hydroxy-3-isopropyl-4-methylpentanenitrile, 3-hydroxy-3-phenylpropanenitrile, 2-propyl-3-hydroxypentanenitrile and 3-hydroxy-3-methyl-n-pentanenitrile. When the 3-hydroxynitrile (or its hydrolysis products) is not completely water miscible, the reaction is run in a two-phase, aqueous/organic reaction mixture as described above, using methods known to those skilled in the art.

In all of the polymerizations described herein to make highly branched copolyesters, wherein at least two repeat units are derived from at least one linear 3-hydroxycarboxylic acid or its ester of the structure $R^1O-CR^4R^5CR^6R^7C(O)OR^1$ and at least one hyperbranching hydroxycarboxylic acid or its ester of the structure $(R^2O)_n$-$R$-$[C(O)OR^1]_m$, wherein R is $C_{1-12}$ hydrocarbyl radical with n+m free valencies, $R^1$ is H, $C_{1-12}$ or hydroxyl substituted $C_{1-12}$ hydrocarbyl radical, $R^3$, $R^4$, $R^5$, $R^6$, $R^7$ is H or $C_{1-12}$ hydrocarbyl radical, $R^2$ is H or $(O)CR^3$, n+m is 3 or more, and provided that one of n and m is 1, these repeat units may also be derived from equivalent compounds that will form polyesters, such as esters of the hydroxycarboxylic acids. The compound $(R^2O)_n$-$R$-$[C(O)OR']_m$, by virtue of being a tri- or higher functional, is sometimes called a hyperbranching monomer. More than one such monomer may be present in such a polymerization. It is preferred that n+m is three or four. Normal esterification catalysts well known in the art may be used with these monomers to form polyesters (for example, a protonic acid, Lewis acid, or a basic catalyst including sulfonic acids, phosphoric and phosphonic acids, titanium alkoxides, dialkyltin oxide, oxides, carbonates and carboxylates of tin, zinc, manganese, calcium, magnesium, or antimony). Methods for making polyesters are well known in the art.

In the following examples, which serve to further illustrate the invention and not to limit it, the % recovery of 3-hydroxynitrile and the % yields of 3-hydroxycarboxylic acid and 3-hydroxycarboxylic acid amide were based on the initial amount of 3-hydroxynitrile present in the reaction mixture. This data was determined by HPLC using a refractive index detector and either a Supelcosil LC-18-DB column (15 cm×4.6 mm diameter) with 7.5% (v/v) methanol in aqueous 10 mM acetic acid/10 mM sodium acetate as mobile phase (for 3-hydroxyvaleronitrile reactions), or a Bio-Rad HPX-87H column (30 cm×7.8 mm diameter) with 0.01 N sulfuric acid as mobile phase (for 3-hydroxypropionitrile reactions). The isolated yields of 3-hydroxyvaleric acid reported in the following examples were not optimized for complete recovery of the product.

EXAMPLES

Materials and methods suitable for the maintenance and growth of bacterial cultures are well known in the art. Techniques suitable for use in the following examples may be found in *Manual of Methods for General Bacteriology*; Phillipp Gerhardt, R. G. E. Murray, Ralph N. Costilow, Eugene W. Nester, Willis A. Wood, Noel R. Krieg and G. Briggs Phillips, Eds.; American Society for Microbiology: Washington, D.C., (1994) or in *Biotechnology: A Textbook of Industrial Microbiology*, 2nd ed.; Thomas D. Brock, Sinauer Associates, Inc.: Sunderland, Mass., (1989). All reagents and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "$\mu L$" means microliters, "mL" means milliliters and "L" means liters.

Comparative Example

Hydrolysis of 3-Hydroxyvaleronitrile with Aqueous Barium Hydroxide According to Ford, *Org. Synth.*, Coll. vol. III: 34–36 (1955)

A 1-liter three-neck round-bottom flask equipped with an overhead stirrer, dropping funnel and heating mantle was charged with barium hydroxide octahydrate (36 g, 0.11 mole), and the flask heated to 91° C. After the barium hydroxide had dissolved in its water of crystallization, 3-hydroxyvaleronitrile (32.7 g, 0.33 mole) was added dropwise at 89° C. After the addition was complete, the reaction mixture was stirred for an additional 40 min. To the flask was then added 15 g of celite and 367 g of distilled water, and the resulting mixture was saturated with carbon dioxide by the addition of 16.2 g of dry ice, while maintaining the reaction mixture at 90° C. The reaction mixture was filtered and the solids returned to the flask, then 200 g of water was added and the mixture heated at 90° C. with stirring for an additional 20 min. The reaction mixture was again filtered and the combined filtrates analyzed by gas chromatography and IR spectroscopy for 3-hydroxyvaleric acid. There was no 3-hydroxyvaleric acid detected in the final product mixture.

Example 1

Hydrolysis of 3-Hydroxyvaleronitrile (0.448 M) with *Comamonas testosteroni* 22-1 Cells (Potassium Phosphate Buffer, pH 7.0)

A 10-mL reaction mixture containing 0.444 g (0.448 M) of 3-hydroxyvaleronitrile and 0.509 g wet cell weight (0.107 g dry cell weight) of *Comamonas testosteroni* 22-1 cells in aqueous potassium phosphate buffer (50 mM, pH 7.0) was mixed at 25° C. Samples (0.100 mL) were mixed with 0.100 mL of distilled, deionized water, then the diluted sample was mixed with 0.200 mL of aqueous 0.200 M sodium butyrate (HPLC external standard) and 0.015 mL of 6 N HCl, centrifuged, and the supernatant analyzed by HPLC. After 2.0 h, the conversion of 3-hydroxyvaleronitrile was 100%, and the yield of 3-hydroxyvaleric acid was 100%.

Example 2

Hydrolysis of 3-Hydroxyvaleronitrile (0.400 M) with *Comamonas testosteroni* 22-1 Cells (Bis-Tris Buffer, pH 6.0)

A 10-mL reaction mixture containing 0.397 g (0.400 M) of 3-hydroxyvaleronitrile and 0.257 g wet cell weight (0.0542 g dry cell weight) of *Comamonas testosteroni* 22-1 cells in aqueous Bis-Tris buffer (50 mM, pH 6.0) was mixed at 25° C. Samples (0.100 mL) were mixed with 0.100 mL of distilled, deionized water, then the diluted sample was mixed with 0.200 mL of aqueous 0.200 M sodium butyrate (HPLC external standard) and 0.015 mL of 6 N HCl, centrifuged, and the supernatant analyzed by HPLC. After 72.0 h, the conversion of 3-hydroxyvaleronitrile was 100%, and the yield of 3-hydroxyvaleric acid was 100%.

Example 3

Hydrolysis of 3-Hydroxyvaleronitrile (0.400 M) with *Comamonas testosteroni* 22-1 Cells (Potassium Phosphate Buffer, pH 8.0)

A 10-mL reaction mixture containing 0.397 g (0.400 M) of 3-hydroxyvaleronitrile and 0.265 g wet cell weight (0.0560 g dry cell weight) of *Comamonas testosteroni* 22-1 cells in aqueous potassium phosphate buffer (50 mM, pH 8.0) was mixed at 25° C. Samples (0.100 mL) were mixed with 0.100 mL of distilled, deionized water, then the diluted sample was mixed with 0.200 mL of aqueous 0.200 M sodium butyrate (HPLC external standard) and 0.015 mL of 6 N HCl, centrifuged, and the supernatant analyzed by HPLC. After 7.5 h, the conversion of 3-hydroxyvaleronitrile was 100%, and the yield of 3-hydroxyvaleric acid was 100%.

Example 4

Hydrolysis of 3-Hydroxyvaleronitrile (0.400 M) with *Comamonas testosteroni* 22-1 Cells (Bicine Buffer, pH 9.0)

A 10-mL reaction mixture containing 0.397 g (0.400 M) of 3-hydroxyvaleronitrile and 0.222 g wet cell weight (0.0468 g dry cell weight) of *Comamonas testosteroni* 22-1 cells in Bicine buffer (50 mM, pH 9.0) was mixed at 25° C. Samples (0.100 mL) were mixed with 0.100 mL of distilled, deionized water, then the diluted sample was mixed with 0.200 mL of aqueous 0.200 M sodium butyrate (HPLC external standard) and 0.015 mL of 6 N HCl, centrifuged, and the supernatant analyzed by HPLC. After 7.5 h, the conversion of 3-hydroxyvaleronitrile was 100%, and the yield of 3-hydroxyvaleric acid was 99%, with no 3-hydroxyvaleric acid amide remaining.

Example 5

Hydrolysis of 3-Hydroxyvaleronitrile (0.400 M) with *Comamonas testosteroni* 22-1 Extract (Potassium Phosphate Buffer, pH 7.0)

A cell extract of *Comamonas testosteroni* 22-1 was prepared by suspending 1.69 g wet cells in 1.69 mL of 0.10 M potassium phosphate buffer (pH 7.0) containing 1 mM dithiothreitol and 0.1 M phenyl methyl sulfonyl fluoride (PMSF), then passing the suspension through a French press. The resulting mixture was centrifuged and the supernatant (2.07 mL of cell extract) decanted from the resulting pellet. A 5-mL reaction mixture containing 0.137 mL of *Comamonas testosteroni* 22-1 cell extract and 0.198 g (0.400 M) of 3-hydroxyvaleronitrile in aqueous potassium phosphate buffer (50 mM, pH 7.0) was mixed at 25° C. Samples (0.100 mL) were mixed with 0.100 mL of distilled, deionized water, then the diluted sample was mixed with 0.200 mL of aqueous 0.200 M sodium butyrate (HPLC external standard) and 0.015 mL of 6 N HCl, centrifuged, and the supernatant analyzed by HPLC. After 45 h, the conversion of 3-hydroxyvaleronitrile was 100%, and the yield of 3-hydroxyvaleric acid was 100%.

Example 6

Hydrolysis of 3-Hydroxyvaleronitrile (1.00 M) with *Comamonas testosteroni* 22-1 Cells (Potassium Phosphate Buffer, pH 7.0)

A 5-mL reaction mixture containing 0.496 g (1.00 M) of 3-hydroxyvaleronitrile and 0.296 g wet cell weight (0.0625 g dry cell weight) of *Comamonas testosteroni* 22-1 cells in potassium phosphate buffer (50 mM, pH 7.0) was mixed at 25° C. Samples (0.100 mL) were mixed with 0.400 mL of distilled, deionized water, then the diluted sample was mixed with 0.200 mL of aqueous 0.200 M sodium butyrate (HPLC external standard) and 0.015 mL of 6 N HCl, centrifuged, and the supernatant analyzed by HPLC. After 24 h, the conversion of 3-hydroxyvaleronitrile was 100%, and the yield of 3-hydroxyvaleric acid was 100%.

Example 7

Hydrolysis of 3-Hydroxyvaleronitrile (2.00 M) with *Comamonas testosteroni* 22-1 Cells (Potassium Phosphate Buffer, pH 7.0)

A 5-mL reaction mixture containing 0.991 g (2.00 M) of 3-hydroxyvaleronitrile and 0.516 g wet cell weight (0.109 g dry cell weight) of *Comamonas testosteroni* 22-1 cells in potassium phosphate buffer (50 mM, pH 7.0) was mixed at 25° C. Samples (0.100 mL) were mixed with 0.900 mL of distilled, deionized water, then the diluted sample was mixed with 0.200 mL of aqueous 0.200 M sodium butyrate (HPLC external standard) and 0.015 mL of 6 N HCl, centrifuged, and the supernatant analyzed by HPLC. After 26.5 h, the conversion of 3-hydroxyvaleronitrile was 100%, and the yields of 3-hydroxyvaleric acid and 3-hydroxyvaleric acid amide were 99% and 1%, respectively.

Example 8

Preparation of 3-Hydroxyvaleric Acid (0.975 M) with *Comamonas testosteroni* 22-1 Cells (No Buffer)

A 100-mL reaction mixture containing 9.66 g (0.975 M) of 3-hydroxyvaleronitrile and 7.20 g wet cell weight of *Comamonas testosteroni* 22-1 cells in distilled water was mixed at 25° C. Samples (0.100 mL) were mixed with 0.900 mL of distilled, deionized water, then the diluted sample was mixed with 0.200 mL of aqueous 0.200 M sodium butyrate (HPLC external standard) and 0.015 mL of 6 N HCl, centrifuged, and the supernatant analyzed by HPLC. Complete conversion of 3-hydroxyvaleronitrile occurred after 5 h, and 3-hydroxyvaleric acid was the only product. The reaction mixture was centrifuged and the supernatant decanted. The cell pellet was washed with 30 mL of water, and the combined wash and supernatant filtered (0.22 micron) and adjusted to pH 1.10 with concentrated HCl. The resulting solution was saturated with sodium chloride, then extracted with ten 100-mL portions of ethyl ether. The combined organic extracts were dried over magnesium sulfate, filtered, and the ether removed by distillation under high vacuum to yield 8.99 g of 3-hydroxyvaleric acid (79% yield).

Example 9

Hydrolysis of 3-Hydroxyvaleronitrile (0.400 M) with *Comamonas testosteroni* 5-MGAM-4D Cells (Potassium Phosphate Buffer, pH 7.0)

A 10-mL reaction mixture containing 0.397 g (0.400 M) of 3-hydroxyvaleronitrile and 0.500 g wet cell weight (0.086 g dry cell weight) of *Comamonas testosteroni* 5-MGAM-4D cells in potassium phosphate buffer (50 mM, pH 7.0) was mixed at 25° C. Samples (0.100 mL) were mixed with 0.100 mL of distilled, deionized water, then the diluted sample was mixed with 0.200 mL of aqueous 0.200 M sodium butyrate (HPLC external standard) and 0.015 mL of 6 N HCl, centrifuged, and the supernatant analyzed by HPLC. After 4.0 h, the conversion of 3-hydroxyvaleronitrile was 100%, and the yield of 3-hydroxyvaleric acid was 100%.

Example 10

Hydrolysis of 3-Hydroxyvaleronitrile (1.00 M) with *Comamonas testosteroni* 5-MGAM-4D Cells (Potassium Phosphate Buffer, pH 7.0)

A 5-mL reaction mixture containing 0.496 g (1.00 M) of 3-hydroxyvaleronitrile and 0.251 g wet cell weight (0.0432 g dry cell weight) of *Comamonas testosteroni* 5-MGAM-4D cells in potassium phosphate buffer (50 mM, pH 7.0) was mixed at 25° C. Samples (0.100 mL) were mixed with 0.400 mL of distilled, deionized water, then the diluted sample was mixed with 0.200 mL of aqueous 0.200 M sodium butyrate (HPLC external standard) and 0.015 mL of 6 N HCl, centrifuged, and the supernatant analyzed by HPLC. After 24 h, the conversion of 3-hydroxyvaleronitrile was 100%, and the yield of 3-hydroxyvaleric acid was 100%.

Example 11

Hydrolysis of 3-Hydroxyvaleronitrile (2.00 M) with *Comamonas testosteroni* 5-MGAM-4D Cells (Potassium Phosphate Buffer, pH 7.0)

A 5-mL reaction mixture containing 0.991 g (2.00 M) of 3-hydroxyvaleronitrile and 0.524 g wet cell weight (0.090 g dry cell weight) of *Comamonas testosteroni* 5-MGAM-4D cells in potassium phosphate buffer (50 mM, pH 7.0) was mixed at 25° C. Samples (0.100 mL) were mixed with 0.900 mL of distilled, deionized water, then the diluted sample was mixed with 0.200 mL of aqueous 0.200 M sodium butyrate (HPLC external standard) and 0.015 mL of 6 N HCl, centrifuged, and the supernatant analyzed by HPLC. After 144 h, the conversion of 3-hydroxyvaleronitrile was 100%, and the yield of 3-hydroxyvaleric acid was 100%.

Example 12

Preparation of 3-Hydroxyvaleric Acid (1.00 M) with *Comamonas testosteroni* 5-MGAM-4D Cells (Potassium Phosphate Buffer, pH 7.0)

A 3-L reaction mixture containing 300 g (1.0 M) of 3-hydroxyvaleronitrile and 134 g wet cell weight of *Comamonas testosteroni* 5-MGAM-4D cells in 20 mM potassium phosphate buffer (pH 7.0) was mixed at 25° C. Samples (0.100 mL) were mixed with 0.900 mL of distilled, deionized water, then the diluted sample was mixed with 0.200 mL of aqueous 0.200 M sodium butyrate (HPLC external standard) and 0.015 mL of 6 N HCl, centrifuged, and the supernatant analyzed by HPLC. Complete conversion of 3-hydroxyvaleronitrile occurred after 46.5 h, and 3-hydroxyvaleric acid was the only product. The reaction mixture was centrifuged and the supernatant decanted. The supernatant was filtered (30,000 molecular weight cut-off), then adjusted to pH 1.9 with concentrated HCl. The resulting solution was saturated with sodium chloride, then extracted with four 1.5-L portions of ethyl ether. The combined organic extracts were dried over magnesium sulfate, filtered, and the ether solution concentrated to 2.4 L by rotary evaporation. Hexanes (1.6 L) was added to the ethyl ether concentrate, and the resulting mixture cooled in dry ice/acetone. The resulting crystalline precipitate was collected by vacuum filtration, washed with cold hexanes, and dried under vacuum to yield 274 g of 3-hydroxyvaleric acid (77% yield; mp 43.0–44.5° C.).

Example 13

Hydrolysis of 3 Hydroxyvaleronitrile with *Acidovorax facilis* 72W Cells (Potassium Phosphate Buffer, pH 7.0)

A 50 wt % cell suspension (0.25 g wet cell weight, 0.060 g dry cell weight) of *Acidovorax facilis* 72W (ATCC 55746) cells in 0.35 M potassium phosphate buffer (pH 7.0) was prepared and subsequently heated at 50° C. for 0.5 h to inactivate nitrile hydratase and amidase activity. A reaction mixture containing 0.50 mL of the heat-treated *Acidovorax facilis* 72W cell suspension (having only nitrilase activity) and 25.4 mg (51.2 mM) of 3-hydroxyvaleronitrile was made up to a total volume of 5.0 mL with 50 mM potassium phosphate buffer (pH 7.0) and mixed at 25° C. Samples (0.100 mL) were mixed with 0.100 mL of distilled, deionized water, then the diluted sample was mixed with 0.200 mL of aqueous 0.200 M sodium butyrate (HPLC external standard) and 0.015 mL of 6 N HCl, centrifuged, and the supernatant analyzed by HPLC. After 18 h, the conversion of 3-hydroxyvaleronitrile was 100%, and the yield of 3-hydroxyvaleric acid was 99%.

Example 14

Hydrolysis of 3-Hydroxyvaleronitrile with *Acidovorax facilis* 72W Cells (Potassium Phosphate Buffer, pH 7.0)

A 5-mL reaction mixture containing 25.1 mg (50.6 mM) of 3-hydroxyvaleronitrile and 0.1926 g wet cell weight (0.046 g dry cell weight) of *Acidovorax facilis* 72W cells (no cell heat-treatment at 50° C. to inactivate nitrile hydratase and amidase activity) in 50 mM potassium phosphate buffer (pH 7.0) was mixed at 25° C. Samples (0.100 mL) were mixed with 0.100 mL of distilled, deionized water, then the diluted sample was mixed with 0.200 mL of aqueous 0.200 M sodium butyrate (HPLC external standard) and 0.015 mL of 6 N HCl, centrifuged, and the supernatant analyzed by HPLC. After 18 h, the conversion of 3-hydroxyvaleronitrile was 100%, and the yields of 3-hydroxyvaleric acid and 3-hydroxyvaleric acid amide were 97% and 3%, respectively.

Example 15

Hydrolysis of 3-Hydroxyvaleronitrile (0.409 M) with *Dietzia sp.* ADL1 Cells (Potassium Phosphate Buffer, pH 7.0)

A 5-mL reaction mixture containing 0.203 g (0.409 M) of 3-hydroxyvaleronitrile and 0.258 g wet cell weight of *Dietzia sp.* ADL1 cells in potassium phosphate buffer (50 mM, pH 7.0) was mixed at 25° C. Samples (0.100 mL) were mixed with 0.100 mL of distilled, deionized water, then the diluted sample was mixed with 0.200 mL of aqueous 0.200 M sodium butyrate (HPLC external standard) and 0.015 mL of 6 N HCl, centrifuged, and the supernatant analyzed by HPLC. After 30 h, the conversion of 3-hydroxyvaleronitrile was 100%, and the yield of 3-hydroxyvaleric acid was 100%.

Example 16

Hydrolysis of 3-Hydroxyvaleronitrile with *Pseudomonas putida* 5B-MGN-2P Cells (Potassium Phosphate Buffer, pH 7.0)

A 5-mL reaction mixture containing 25.0 mg (50.4 mM) of 3-hydroxyvaleronitrile and 0.258 g wet cell weight of *Pseudomonas putida* 5B-MGN-2P cells in potassium phosphate buffer (50 mM, pH 7.0) was mixed at 25° C. Samples (0.100 mL) were mixed with 0.100 mL of distilled, deionized water, then the diluted sample was mixed with 0.200 mL of aqueous 0.200 M sodium butyrate (HPLC external standard) and 0.015 mL of 6 N HCl, centrifuged, and the supernatant analyzed by HPLC. After 47 h, the conversion of 3-hydroxyvaleronitrile was 100%, and the yields of 3-hydroxyvaleric acid and 3-hydroxyvaleric acid amide were 96% and 1.1%, respectively.

Example 17

Hydrolysis of 3-Hydroxyvaleronitrile with *Scytalidium spp.* 3LD-122P Cells (Potassium Phosphate Buffer, pH 7.0)

A 5-mL reaction mixture containing 25.7 mg (51.9 mM) of 3-hydroxyvaleronitrile and 0.339 g wet cell weight of *Scytalidium spp.* 3LD-122P cells in potassium phosphate buffer (50 mM, pH 7.0) was mixed at 25° C. Samples (0.100 mL) were mixed with 0.100 mL of distilled, deionized water, then the diluted sample was mixed with 0.200 mL of aqueous 0.200 M sodium butyrate (HPLC external standard) and 0.015 mL of 6 N HCl, centrifuged, and the supernatant analyzed by HPLC. After 75 h, the conversion of 3-hydroxyvaleronitrile was 100%, and the yield of 3-hydroxyvaleric acid was 100%.

Example 18

Hydrolysis of 3-Hydroxyvaleronitrile with *Rhodococcus sp.* 25-1 Cells (Potassium Phosphate Buffer, pH 7.0)

A 10-mL reaction mixture containing 99.2 mg (100 mM) of 3-hydroxyvaleronitrile and 0.50 g wet cell weight of Rhodococcus sp. 25-1 cells in potassium phosphate buffer (20 mM, pH 7.0) was mixed at 25° C. Samples (0.300 mL) were mixed with 0.032 mL of 6 N HCl, filtered (10,000 molecular weight cutoff), and the filtrate analyzed by HPLC. After 1 h, the conversion of 3-hydroxyvaleronitrile was 100%, and 3-hydroxyvaleric acid was the only observed product produced at approximately 100 mM concentration.

Example 19

Immobilization of Cells in Calcium Alginate

Example 19 illustrates a typical immobilization of cells in GA/PEI-crosslinked calcium alginate.

Into a 250-mL media bottle equipped with magnetic stir bar and containing 68.7 g of distilled, deionized water at 50° C. was slowly added 3.30 g of FMC BioPolymer Protanal® LF 10/60 alginate with rapid stirring. The mixture was heated to 75–80° C. with rapid stirring until the alginate was completely dissolved, and the resulting solution cooled to 25° C. in a water bath. A suspension of *Comamonas testosteroni* 22-1 cells (28.6 g wet cell weight, 21% dry cell weight) in 0.185 M sodium acetate buffer (19.4 mL, pH 7.0) was prepared at 25° C. and added to the alginate solution at 25° C. with stirring. The cell/alginate mixture was added dropwise by syringe to 640 mL of 0.20 M calcium acetate buffer (pH 7.0) at 25° C. with stirring. After stirring for 2 h, the buffer was decanted from the resulting beads, which were resuspended in 293 mL of 0.20 M calcium acetate buffer (pH 7.0) at 25° C. With stirring, 6.0 g of 25 wt % glutaraldehyde (GA) in water was added and the beads mixed for 1.0 h at 25° C. To the suspension was then added 24.0 g of 12.5 wt % polyethylenimine (PEI) (BASF Lupasol® PR971L, average molecular weight ca. 750,000) in water, and the beads mixed for an additional 1 h at 25° C. The crosslinked beads were then washed twice with 300 mL of 0.20 M calcium acetate buffer (pH 7.0) at 25° C., and stored in this same buffer at 5° C.

Example 20

Hydrolysis of 3-Hydroxyvaleronitrile (1.0 M) with Immobilized *Comamonas testosteroni* 22-1 Cells (No Buffer)

Into a 50-mL jacketed reaction vessel (temperature-controlled at 15° C. with a recirculating temperature bath) was placed 4.0 g of GA/PEI-crosslinked *Comamonas testosteroni* 22-1 cell/alginate beads prepared as described in Example 19. To the reaction vessel was added 13.45 mL of distilled, deionized water, 0.5 mL of 0.20 M calcium acetate buffer (pH 7.0, 5.0 mM final calcium ion concentration in reaction mixture) and 2.05 mL (1.98 g, 1.0 M) of 3-hydroxyvaleronitrile, and the mixture stirred at 15° C. Samples (0.100 mL) of the reaction mixture were mixed with 0.400 mL of water, and then 0.200 mL of the diluted sample was mixed with 0.200 mL of 0.200 M sodium butyrate (HPLC external standard) in water and 0.020 mL of 6.0 N glacial acetic acid. The resulting sample was centrifuged, and the supernatant analyzed by HPLC. After 24.25 h, the conversion of 3-hydroxyvaleronitrile was 100%, and the yield of 3-hydroxyvaleric acid was 99.8%.

Example 21

Hydrolysis of 3-Hydroxyvaleronitrile (1.0 M) with Immobilized *Comamonas testosteroni* 5-MGAM-4D Cells (No Buffer)

Into a 50-mL jacketed reaction vessel (temperature-controlled at 25° C. with a recirculating temperature bath) was placed 4.0 g of GA/PEI-crosslinked *Comamonas testosteroni* 5-MGAM-4D cell/alginate beads prepared by the method described in Example 19. To the reaction vessel was added 13.45 mL of distilled, deionized water, 0.5 mL of 0.20 M calcium acetate buffer (pH 7.0, 5.0 mM final calcium ion concentration in reaction mixture) and 2.05 mL (1.98 g, 1.0 M) of 3-hydroxyvaleronitrile, and the mixture stirred at 25° C. Samples (0.100 mL) of the reaction mixture were mixed with 0.400 mL of water, and then 0.200 mL of the diluted sample was mixed with 0.200 mL of 0.200 M sodium butyrate (HPLC external standard) in water and 0.020 mL of 6.0 N glacial acetic acid. The resulting sample was centrifuged, and the supernatant analyzed by HPLC. After 7 h, the conversion of 3-hydroxyvaleronitrile was 100%, and the yield of 3-hydroxyvaleric acid was 100%.

At the end of the reaction the product mixture was decanted from the catalyst beads. The catalyst was reused in a further three consecutive batch reactions under the conditions as described above; reactions 2, 3, and 4 produced yields of 3-hydroxyvaleric acid of 99.7%, 99.7%, and 99.6% in 9 h, 9 h, and 5 h, respectively. At the completion of the four recycle reactions, the final concentration of 3-hydroxyvaleric acid in the final product mixture was 1.29 M.

Example 22

Hydrolysis of 3-Hydroxyvaleronitrile (1.0 M) with Immobilized *Dietzia* sp. ADL1 Cells (No Buffer)

Into a 50-mL jacketed reaction vessel (temperature-controlled at 25° C. with a recirculating temperature bath) was placed 4.0 g of GA/PEI-crosslinked *Dietzia* sp. ADL1 cell/alginate beads prepared by the method described in Example 19. To the reaction vessel was added 13.45 mL of distilled, deionized water, 0.5 mL of 0.20 M calcium acetate buffer (pH 7.0, 5.0 mM final calcium ion concentration in reaction mixture), and 2.05 mL (1.98 g, 1.0 M) of 3-hydroxyvaleronitrile, and the mixture stirred at 25° C. Samples (0.100 mL) of the reaction mixture were mixed with 0.400 mL of water, and then 0.200 mL of the diluted sample was mixed with 0.200 mL of 0.200 M sodium butyrate (HPLC external standard) in water and 0.020 mL of 6.0 N glacial acetic acid. The resulting sample was centrifuged, and the supernatant analyzed by HPLC. After 23 h, the conversion of 3-hydroxyvaleronitrile was 100%, and the yield of 3-hydroxyvaleric acid was 98.6%.

Example 23

Hydrolysis of 3-Hydroxypropionitrile (0.100 M) with *Comamonas testosteroni* 22-1 Cells (Potassium Phosphate Buffer pH 7.0)

A 10-mL reaction mixture containing 0.0711 g (0.100 M) of 3-hydroxypropionitrile and 0.38 g wet cell weight (0.080 g dry cell weight) of *Comamonas testosteroni* 22-1 cells in aqueous potassium phosphate buffer (50 mM, pH 7.0) was mixed at 25° C. Samples (0.200 mL) were mixed with 0.200 mL of aqueous 0.200 M sodium butyrate (HPLC external standard) and 0.020 mL of 6 N acetic acid, centrifuged, and the supernatant analyzed by HPLC. After 1.0 h, the conversion of 3-hydroxypropionitrile was 100%, and the yield of 3-hydroxypropionic acid was 100%.

Example 24

Hydrolysis of 3-Hydroxypropionitrile (0.400 M) with *Comamonas testosteroni* 22-1 Cells (Potassium Phosphate Buffer, pH 7.0)

A 10-mL reaction mixture containing 0.2843 g (0.400 M) of 3-hydroxypropionitrile and 0.38 g wet cell weight (0.080 g dry cell weight) of *Comamonas testosteroni* 22-1 cells in aqueous potassium phosphate buffer (50 mM, pH 7.0) was mixed at 25° C. Samples (0.200 mL) were mixed with 0.200 mL of aqueous 0.200 M sodium butyrate (HPLC external standard) and 0.020 mL of 6 N acetic acid, centrifuged, and the supernatant analyzed by HPLC. After 1.0 h, the conversion of 3-hydroxypropionitrile was 100%, and the yield of 3-hydroxypropionic acid was 99%.

Example 25

Hydrolysis of 3-Hydroxypropionitrile (1.00 M) with *Comamonas testosteroni* 22-1 Cells (Potassium Phosphate Buffer, pH 7.0)

A 10-mL reaction mixture containing 0.7108 g (1.00 M) of 3-hydroxypropionitrile and 0.44 g wet cell weight (0.092 g dry cell weight) of *Comamonas testosteroni* 22-1 cells in aqueous potassium phosphate buffer (50 mM, pH 7.0) was mixed at 25° C. Samples (0.200 mL) were mixed with 0.200 mL of aqueous 0.200 M sodium butyrate (HPLC external standard) and 0.020 mL of 6 N acetic acid, centrifuged, and the supernatant analyzed by HPLC. After 15.0 h, the conversion of 3-hydroxypropionitrile was 100%, and the yield of 3-hydroxypropionic acid was 100%.

Example 26

Hydrolysis of 3-Hydroxypropionitrile (0.100 M) with *Comamonas testosteroni* 5-MGAM-4D Cells (Potassium Phosphate Buffer, pH 7.0)

A 10-mL reaction mixture containing 0.0711 g (0.100 M) of 3-hydroxypropionitrile and 0.37 g wet cell weight (0.070 g dry cell weight) of *Comamonas testosteroni* 5-MGAM-4D cells in aqueous potassium phosphate buffer (50 mM, pH 7.0) was mixed at 25° C. Samples (0.200 mL) were mixed with 0.200 mL of aqueous 0.200 M sodium butyrate (HPLC external standard) and 0.020 mL of 6 N acetic acid, centrifuged, and the supernatant analyzed by HPLC. After 1.0 h, the conversion of 3-hydroxypropionitrile was 100%, and the yield of 3-hydroxypropionic acid was 100%.

Example 27

Hydrolysis of 3-Hydroxypropionitrile (0.400 M) with *Comamonas testosteroni* 5-MGAM-4D Cells (Potassium Phosphate Buffer, pH 7.0)

A 10-mL reaction mixture containing 0.2843 g (0.400 M) of 3-hydroxypropionitrile and 0.39 g wet cell weight (0.074 g dry cell weight) of *Comamonas testosteroni* 5-MGAM-4D cells in aqueous potassium phosphate buffer (50 mM, pH 7.0) was mixed at 25° C. Samples (0.200 mL) were mixed with 0.200 mL of aqueous 0.200 M sodium butyrate (HPLC external standard) and 0.020 mL of 6 N acetic acid, centrifuged, and the supernatant analyzed by HPLC. After 1.0 h, the conversion of 3-hydroxypropionitrile was 100%, and the yield of 3-hydroxypropionic acid was 100%.

Example 28

Hydrolysis of 3-Hydroxypropionitrile (1.00 M) with *Comamonas testosteroni* 5-MGAM-4D Cells (Potassium Phosphate Buffers pH 7.0)

A 10-mL reaction mixture containing 0.7108 g (1.00 M) of 3-hydroxypropionitrile and 0.42 g wet cell weight (0.079 g dry cell weight) of *Comamonas testosteroni* 5-MGAM-4D cells in aqueous potassium phosphate buffer (50 mM, pH 7.0) was mixed at 25° C. Samples (0.200 mL) were mixed with 0.200 mL of aqueous 0.200 M sodium butyrate (HPLC external standard) and 0.020 mL of 6 N acetic acid, centrifuged, and the supernatant analyzed by HPLC. After 15.0 h, the conversion of 3-hydroxypropionitrile was 100%, and the yield of 3-hydroxypropionic acid was 100%.

Example 29

Hydrolysis of 3-Hydroxynitriles with *Comamonas testosteroni* 5-MGAM-4D Cells (Potassium Phosphate Buffer, pH 7.0)

A 10-mL reaction mixture containing from 0.100 M to 1.0 M of a 3-hydroxynitrile (listed in the table below) and 0.37 g wet cell weight (0.070 g dry cell weight) of *Comamonas testosteroni* 5-MGAM-4D cells in aqueous potassium phosphate buffer (50 mM, pH 7.0) is mixed at 25° C. Samples (0.200 mL) are mixed with 0.200 mL of aqueous HPLC external standard and 0.020 mL of 6 N acetic acid, centrifuged, and each supernatant is analyzed by HPLC. At complete conversion of 3-hydroxynitrile, the yield of 3-hydroxycarboxylic acid is expected to be from 99% to 100%.

TABLE 7

| 3-Hydroxynitriles |
| --- |
| 3-hydroxybutyronitrile |
| 3-hydroxyhexanenitrile |
| 3-hydroxyheptanenitrile |
| 3-hydroxyoctanenitrile |
| 3-hydroxynonanenitrile |
| 3-hydroxy-3-isopropyl-4-methylpentanenitrile |
| 3-hydroxy-3-phenylpropanenitrile |
| 2-propyl-3-hydroxypentanenitrile |
| 3-hydroxy-3-methyl-n-pentanenitrile |
| 3-hydroxy-4-methylpentanenitrile |
| 3-hydroxy-4-pentenenitrile |

Example 30

Synthesis of Highly Branched Copolyester from 3-Hydroxyvaleric Acid and Dimethylolpropionic Acid with Tin (II) Catalyst In a 500 mL three-neck flask equipped with a mechanical stirrer, thermocouple, short path distillation head with a water condenser under nitrogen flow, was placed dimethylolpropionic acid (50 g, 0.37 mole), 3-hydroxyvaleric acid (49.6 g, 0.42 mole), tin (II) di (2-ethylhexanoate) (Sn $(O_2CC_7H_{15})_2$ (1 g, 0.0025 mole), and xylenes (10 g) and heated at 180° C. The reaction progress was monitored by the acid number measurements and by the water volume collected. After 12 h, 14 mL water was collected, 1 g sample was withdrawn, dissolved in 10 mL dimethyl sulfoxide and the acid number (17) was determined by titration with 0.1 N potassium hydroxide in methanol. The reaction was stopped (heat off) after a total of 21 h, when the acid number was 5.8. The hot viscous clear yellow polymer was poured out of the reactor. The polymer had $M_w$ 19,100 as determined by gel permeation chromatography versus polystyrene standards in dimethylacetamide at 135° C., intrinsic viscosity 0.101, $T_g$=0° C. by differential scanning calorimetry, which was desirably significantly higher than $T_g$=−28° C. of the analogous copolymer where ε-caprolactone was used in place of 3-hydroxyvaleric acid.

Example 31

Synthesis of Highly Branched Copolyester From 3-Hydroxyvaleric Acid and Dimethylolpropionic Acid with a Protonic Acid Catalyst In a 500 mL three-neck flask equipped with a mechanical stirrer, thermocouple, short path distillation head with a water condenser under nitrogen flow, was placed dimethylolpropionic acid (50 g, 0.37 mole), 3-hydroxyvaleric acid (49.6 g, 0.42 mole), dodecylbenzenesulfonic acid (0.3 g, 0.00092 mole), and xylenes (10 g) and heated at 172° C. for 20 min until melted and then heating was reduced to 140° C. The reaction progress was monitored by the acid number measurements and by the water volume collected. After 12 h, 9 mL water was collected, 1 g sample was withdrawn, dissolved in 10 mL dimethyl sulfoxide and the acid number (106) was determined by titration with 0.1 N potassium hydroxide in methanol. After 14 h, the reaction temperature was raised to 160° C. Acid numbers were 100 after a total of 17 h and 68 after a total of 40 h. After a total of 43 h, the reaction temperature was raised to 180° C. The reaction was stopped (heat off) after a total of 57 h, when the acid number was 49. The hot viscous clear yellow polymer was poured out of the reactor. The polymer had $M_w$ 4,200 as determined by gel permeation chromatography versus polystyrene standards in dimethylacetamide at 135° C., intrinsic viscosity 0.0045, $T_g$=−13° C. by differential scanning calorimetry, which was desirably significantly higher than $T_g$=−28° C. of the analogous copolymer where ε-caprolactone was used in place of 3-hydroxyvaleric acid.

Example 32

Synthesis of Highly Branched Copolyester from 3-Hydroxy-2,2-dimethylpropionic Acid and Dimethylolpropionic Acid with Tin (II) Catalyst In a 500 mL three-neck flask equipped with a mechanical stirrer, thermocouple, short path distillation head with a water condenser under nitrogen flow, was placed dimethylolpropionic acid (100 g, 0.74 mole), 3-hydroxy-2,2-dimethylpropyl-3-hydroxy-2,2-dimethylpropionate (200 g, 0.98 mole), tin (II) di (2-ethylhexanoate) $(Sn(O_2CC_7H_{15})_2$ (2 g, 0.005 mole), and xylenes (10 g) and heated at 180° C. The reaction progress was monitored by the acid number measurements and by the water volume collected. The reaction was stopped (heat off) after a total of 12 h, 20 mL water was collected, 1 g sample was withdrawn, dissolved in 10 mL dimethyl sulfoxide and the acid number (1.1) was determined by titration with 0.1 N potassium hydroxide in methanol. The hot viscous clear polymer was poured out of the reactor. The polymer had $M_w$ 1,400, polydispersity 2.9 as determined by gel permeation chromatography versus polystyrene standards in dimethylacetamide at 135° C., intrinsic viscosity 0.019, $T_g$=−28° C. by differential scanning calorimetry, which was desirably higher than $T_g$=−38° C. of the analogous copolymer where ε-caprolactone was used in place of 3-hydroxy-2,2-dimethylpropyl-3-hydroxy-2,2-dimethylpropionate.

Example 33

Synthesis of Highly Branched Copolyester from 3-Hydroxyvaleric Acid and Trimethylolacetic Acid with Tin (II) Catalyst In a 20 mL glass vial, was placed trimethylolacetic acid (1 g, 0.0067 mole), 3-hydroxyvaleric acid (1 g, 0.0085 mole), tin (II) di (2-ethylhexanoate) $(Sn(O_2CC_7H_{15})_2$ (0.01 g, 0.000025 mole) and heated at 150° C. in a vacuum oven at 20 in. Hg vacuum. The reaction progress was monitored by the acid number measurements. The reaction was stopped (heat off) after a total of 3.5 h, 0.1 g sample was withdrawn, dissolved in dimethyl sulfoxide and the acid number (112) was determined by titration with 0.1 N potassium hydroxide in methanol. The clear polymer had $T_g$=−3° C. by differential scanning calorimetry, which was desirably higher than $T_g$=−32° C. of the analogous copolymer where ε-caprolactone was used in place of 3-hydroxyvaleric acid.

What is claimed is:

1. A process for hydrolyzing 3-hydroxynitrile to 3-hydroxycarboxylic acid comprising the steps of:
    (a) contacting a 3-hydroxynitrile selected from the group consisting of 3-hydroxypropionitrile, 3-hydroxybutyronitrile, 3-hydroxyvaleronitrile, 3-hydroxyhexanenitrile, 3-hydroxyheptanenitrile, 3-hydroxynonanenitrile, 3-hydroxy-3-isopropyl-4-methylpentanenitrile, 3-hydroxy-3-phenylpropanenitrile, 2-propyl-3-hydroxypentanenitrile, and 3-hydroxy-3-methyl-n-pentanenitrile in an aqueous reaction mixture with an e catalyst characterized by
        1) nitrile hydratase and amidase activity of microbial cells selected from the group consisting of Acidovorax facilis 72W (ATCC 55746), Comamonas testosteroni 22-1 (ATCC PTA-1853), Comamonas testosteroni 5-MGAM-4D (ATCC 55744), Dietzia sp. ADL1 (ATCC PTA-1854), Syctalidium spp. 3LD-122P (ATCC PTA-1855), Rhodococcus sp. 25-1 (ATCC PTA-1856), and Pseudomonas putida 5B-MGN-2P (NRRL-B-18668); or
        2) nitrilase activity of microbial cells selected from the group consisting of Acidovorax facilis 72-PF-15 (ATCC 55747), Acidovorax facilis 72-PF-17 (ATCC 55745), and Acidovorax facilis 72W (ATCC 55746), the Acidovorax facilis 72W (ATCC 55746) heat-treated to inactivate nitrile hydratase and amidase activities; and
    (b) optionally, recovering the 3-hydroxycarboxylic acid produced in step (a).

2. The process of claim 1 wherein the enzyme catalyst is in the form of whole microbial cells, permeabilized microbial cells, one or more components of a microbial cell extract, partially purified enzyme(s), or purified enzyme(s).

3. The process of claim 2 wherein the enzyme catalyst is immobilized on or in a soluble or insoluble support.

4. A process for preparing 3-hydroxyvaleric acid comprising the steps of:
    (a) contacting 3-hydroxyvaleronitrile in an aqueous reaction mixture with an enzyme catalyst characterized by
        1) nitrile hydratase activity and amidase activity of microbial cells selected from the group consisting of Acidovorax facilis 72W (ATCC 55746), Comamonas testosteroni 22-1(ATCC PTA-1853), Comamonas testosteroni 5-MGAM-4D (ATCC 55744), Dietzia sp. ADL1 (ATCC PTA-1854), Syctalidium spp. 3LD-122P (ATCC PTA-1855), Rhodococcus sp. 25-1 (ATCC PTA-1856), and Pseudomonas putida 5B-MGN-2P (NRRL-B-18668); or
        2) nitrilase activity of microbial cells selected from the group consisting of Acidovorax facilis 72-PF-15 (ATCC 55747), Acidovorax facilis 72-PF-17 (ATCC 55745), and Acidovorax facilis 72W (ATCC 55746), the Acidovorax facilis 72W (ATCC 55746) heat-treated to inactivate nitrile hydratase and amidase activities; and
    (b) optionally, recovering 3-hydroxyvaleric acid produced in step (a).

5. The process of claim 4 wherein the enzyme catalyst is in the form of whole microbial cells, permeabilized microbial cells, one or more components of a microbial cell extract, partially purified enzyme s), or purified enzyme(s).

6. The process of claim 5 wherein the enzyme catalyst is immobilized on or in a soluble or insoluble support.

* * * * *